US00PP08337P

United States Patent [19]

de Ruiter

[11] Patent Number: Plant 8,337

[45] Date of Patent: Aug. 10, 1993

[54] HYBRID TEA ROSE PLANT NAMED RUIHANO

[75] Inventor: Gijsbert de Ruiter, Hazerswoude, Netherlands

[73] Assignee: De Ruiter's Nieuwe Rozen B.V., Hazerswoude, Netherlands

[21] Appl. No.: 904,516

[22] Filed: Jun. 25, 1992

[51] Int. Cl.[5] ..... A01H 5/00

[52] U.S. Cl. ..... Plt./18

[58] Field of Search ..... Plt./11, 18, 17, 19

*Primary Examiner*—Howard J. Locker

*Attorney, Agent, or Firm*—Christie, Parker & Hale

[57] ABSTRACT

A new variety of hybrid tea rose plant having light pink flowers and suitable for greenhouse growing.

1 Drawing Sheet

SUMMARY OF THE INVENTION

The present invention relates to a new and distinct variety of rose plant of the hybrid tea rose class, which was originated by me by crossing as the seed parent the variety known as 'Ruimeva' U.S. Plant Pat. No. 5,820 and as pollen parent the variety known as 'Korflug' U.S. Plant Pat. No. 5,575. The varietal denomination of the new variety is 'Ruihano'.

Among the novel characteristics possessed by this new variety which distinguishes it from its parent and all other varieties of which I am aware are its light pink flowers borne on a plant particularly suited for production of cut flowers under glass. The new variety can be reproduced through propagation by cuttings, grafting, budding and micropropagation. Flowers of the new variety are long lasting on the plant and after cutting. Asexual reproduction by budding, grafting, propagation of cuttings and micropropagation of the new variety as performed in Hazerswoude, Holland, shows that the foregoing and other distinguishing characteristics come true to form and are established and transmitted through succeeding propagations.

BRIEF DESCRIPTION OF ILLUSTRATIONS

The accompanying illustration shows typical specimens of the vegetative growth and flowers of the new variety in different stages of development depicted in color as nearly true as it is reasonably possible to make the same in a color illustration of this character. Phenotypic expression, including color, may vary depending upon growing conditions such as climatic, soil, and cultivation conditions.

DETAILED DESCRIPTION OF THE NEW VARIETY

The following is a detailed description of the new variety, with color terminology in accordance with The Royal Horticultural Society Colour Chart (R.H.S.C.C.) and horticultural terminology in accordance with standard terminology used in UPOV-approved horitcultural guidelines. The terminology used in color descriptions herein refers to plate numbers in the aforementioned color chart.

Parentage: Seedling.

*Seed parent.*—'Ruimeva' U.S. Plant Pat. No. 5,820.

*Pollen parent.*—'Korflug' U.S. Plant Pat. No. 5,575

Class: Hybrid tea.

The accompanying illustration depicts the top of a young shoot, 1; compound three and five leaflet leaves, 2 and 3, respectively; a stem, 5; buds, 6 and 7; a flower, 8, about one-half open; and a flower 9, more fully open. Also shown are flower stems 10, 11 and 12, with reproductive organs.

The following further horticultural observations were made of specimens grown under glass in Holland.

FLOWER

Blooming Habit: Nearly continuous.

A. Bud:

(1) *Size.*—Medium.

(2) *Form.*—Ovate (just before separation of sepals); urn shaped after sepals part.

(3) *Color.*—As sepals divide, bud color is near 39D with yellow-green cast.

(4) *Sepals.*—Slightly longer than bud, simple to slightly foliated.

(5) *Peduncle.*—Length — medium. Aspect — straight. Strength — erect. Color — medium green.

Bloom: Flower: Large size for cut flower hybrid tea; viewed from above — round; viewed from side — (a) upper part of fully opened flower, flattened convex; (b) lower part of fully opened flower, flattened convex.

(1) *Size.*—Average size when fully expanded — about 13 to 14 cm.

(2) *Borne.*—Singly, primarily one to a stem (3) *Form.*—Ovate bud becomes urn shaped as petals begin to unfurl then flower becomes flat upon opening; outer petals reflex and inner petals roll under.

(4) *Petalage.*—About 37 petals under normal conditions — fully semi-double.

(5) *Color.*—After sepals separate, bud is near 39D with yellow-green cast; when sepals part and petals begin to unfurl, color is near 39D; petals' top surface near 49C-49B with near 48D-C where petals bunch; reverse sides very pale pink but with apricot pink blush. Coloring at point of petal attachment is near 8B. Overall tonality from a distance is attractive light pink.

(6) *Pedicel.*—Medium number hairs or prickles.

(7) *Fragrance.*—Weak.

C. Petals:

(1) *Texture.*—Medium.

(2) *Appearance.*—Inside velvety and outside satiny.
(3) *Form and size.*—Large to very large, transverse elliptic.
(4) *Arrangement.*—Regularly arranged, imbricated.
(5) *Petaloids in center.*—Few.
(6) *Lasting quality.*—Long lasting quality on plant and after cutting.

REPRODUCTIVE ORGANS

A. Stamens, filaments and anthers:
*Arrangement and color.*—Regularly arranged around styles; color of filaments — pink.
B. Pollen:
*Color.*—Yellow orange.
C. Styles: Medium, red, hairy.
D. Stigmas: Positioned at about the same level as anthers.
E. Hips: Medium, pitcher-shaped.

PLANT

A. Form: Upright to bushy.
B. Growth: Vigorous, average height about 1.6 meters.
C. Foliage: Compound 3, and 5 leaflets.
(1) *Size.*—Medium.
(2) *Quantity.*—Abundant.
(3) *Color.*—Foliage at time of first flowering — dark green.
(4) *Shape.*—Oval, pointed.
(5) *Texture.*—Upper side is semi-glossy; underside is matte.
(6) *Edge.*—Serrate.
(7) *Serration.*—Ordinary, acuminate apices.
(8) *Leaf stem.*—Color — medium green.
(9) *Stipules.*—Short, simple, medium to light green, distinct auricle.
(10) *Leaflets.*—Cross section — flat, weak undulation at margin; terminal leaflet (length of blade) — medium length, medium width; petiole — medium, base rounded.
D. Wood:
(1) *New wood.*—Color — reddish brown, young shoots have medium anthocyanin coloration.
(2) *Old wood.*—Color — medium green.
(3) *Typical flower stem length.*—About 60 cm.
E. Prickles (Thorns):
(1) *Prickles.*—Present; quantity (main stalk) — ordinary; On laterals from stalk — ordinary; Form — straight; Shape of upper side — flat Shape of lower side — deep concave Length — few $\leqq 5$ mm; medium $> 5$ mm. Color — tan to greenish tan. Position — irregular.

I claim:

1. A new and distinct variety of rose plant of the hybrid tea rose class, substantially as shown and described.

* * * * *

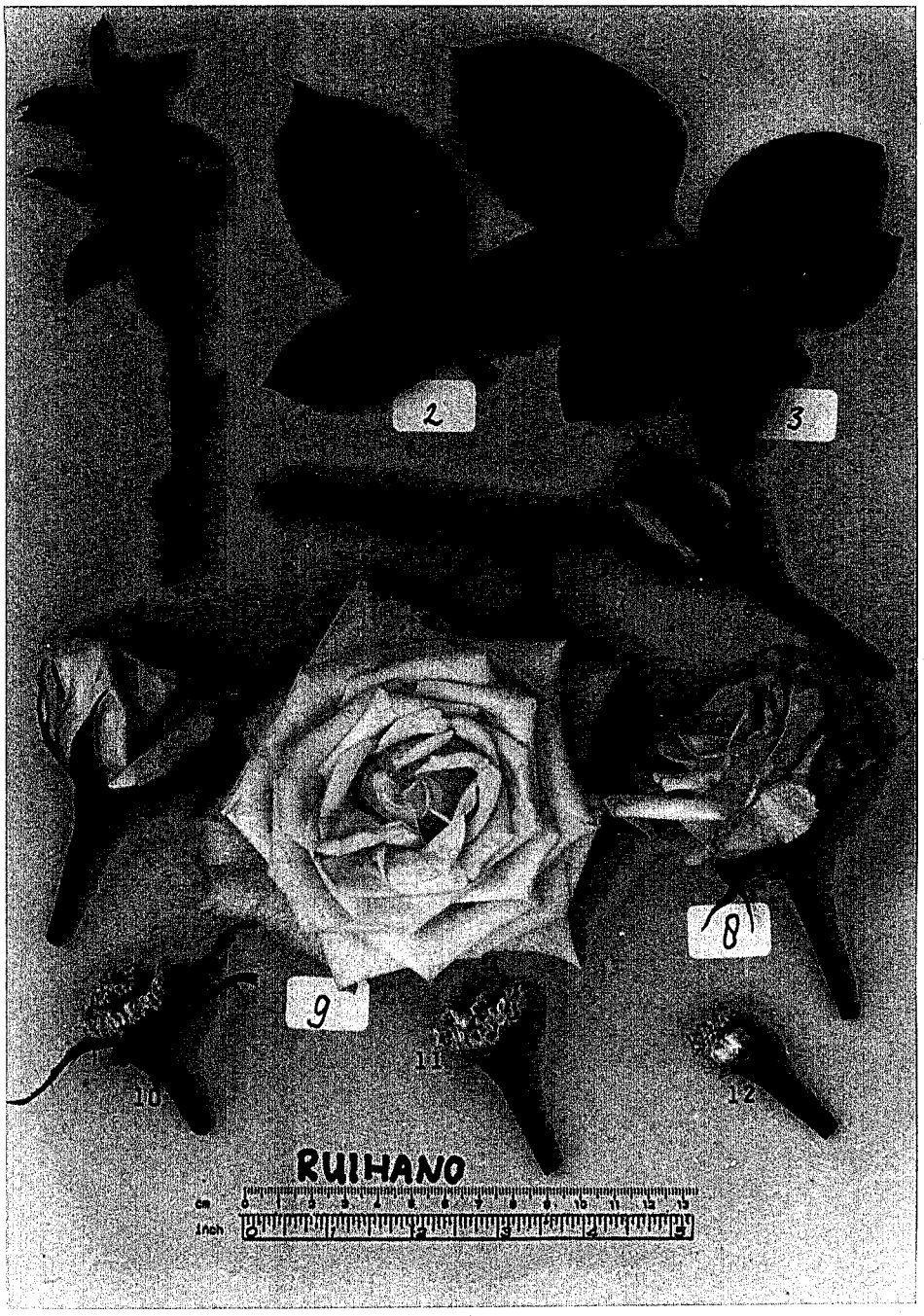
2
3
8
9
10
11
12
RUIHANO
cm
inch